United States Patent [19]

Kajimoto

[11] 4,257,967
[45] Mar. 24, 1981

[54] CATALYST COMPOSITION AND METHOD FOR OXIDATION OF ETHYLENE TO ETHYLENE OXIDE AND METHOD OF CATALYST MANUFACTURE

[75] Inventor: Tsunesuke Kajimoto, Kamakura, Japan

[73] Assignee: Toray Industries, Inc., Tokyo, Japan

[21] Appl. No.: 36,066

[22] Filed: May 4, 1979

[30] Foreign Application Priority Data

Nov. 1, 1978 [JP] Japan .................................. 53-134989

[51] Int. Cl.$^3$ ...................... C07D 301/10; B01J 23/10; B01J 23/50; B01J 27/20
[52] U.S. Cl. .............................. 260/348.34; 252/437; 252/438; 252/440; 252/443; 252/462; 252/476
[58] Field of Search ............... 252/437, 438, 440, 443, 252/462, 476; 260/348.34

[56] References Cited

U.S. PATENT DOCUMENTS

| 3,463,781 | 8/1969 | Bell et al. | 252/443 X |
| 3,836,481 | 9/1974 | Kajimoto et al. | 252/462 |
| 3,899,445 | 8/1975 | Kajimoto et al. | 252/462 |

Primary Examiner—W. J. Shine
Attorney, Agent, or Firm—Miller & Prestia

[57] ABSTRACT

A catalyst composition is provided comprising reduced silver combined with at least one carbonate of a rare earth metal and yttrium, at least one salt of an alkali or alkaline earth metal, and a catalyst carrier, wherein the carbonate is prepared by the reaction of a chloride of a rare earth metal or yttrium with an alkali carbonate or bicarbonate. The catalyst shows high selectivity in the oxidation of ethylene to ethylene oxide in the presence of the catalyst and molecular oxygen.

41 Claims, No Drawings

CATALYST COMPOSITION AND METHOD FOR OXIDATION OF ETHYLENE TO ETHYLENE OXIDE AND METHOD OF CATALYST MANUFACTURE

The present invention relates to a catalyst composition and method, and to a method for the oxidation of ethylene by molecular oxygen to ethylene oxide. More particularly it relates to a silver catalyst composition containing a specified moderator, to a method of making the catalyst, and to a method of oxidizing ethylene in the presence of said catalyst composition.

A commonly employed process for the production of ethylene oxide comprises oxidizing ethylene in the vapor phase with molecular oxygen over a silver catalyst. Catalysts previously employed did not necessarily give satisfactory results, especially in respect of selectivity to ethylene oxide.

Various moderators and promotors have been proposed to be added to a silver catalyst in order to give high selectivity, high catalytic activity and long catalyst life.

Silver catalysts provided with a moderator of rare earth metal such as lanthanum, cerium, praseodymium, neodymium, samarium, europium, gadolinium, terbium, dysprosium, holmium, erbium, thulium, ytterbium and lutetium or yttrium have been proposed in U.S. Pat. Nos. 3,836,481 and 3,899,445. In those references hydroxides, nitrates, and/or oxalates are used as moderators of the rare earth metal or yttrium. The catalysts containing hydroxides of rare earth metals or yttrium gave somewhat high selectivities in the production of ethylene oxide, but they were not necessarily satisfactory in regard to selectivity and catalytic life.

We now have found that carbonates derived from chlorides are more effective as moderators for improving selectivity and catalytic life of silver catalysts for the oxidation of ethylene to ethylene oxide and that their characteristics represent a sharp improvement over the hydroxide or even carbonate moderators otherwise prepared.

The catalyst composition of the present invention comprises reduced silver (A) and at least one carbonate (B) of a metal selected from the group consisting of the rare earth metals and yttrium prepared by the reaction of a chloride (E) of said metal with an alkali metal carbonate or bicarbonate (F), said (A) and (B) being supported together with at least one salt (C) of a metal selected from the group consisting of the alkali and alkaline earth metals on a catalyst carrier (D) having a surface area of less than about 10 m$^2$/g.

The reduced silver used in making the catalyst of the present invention may be produced by conventional methods such as the reduction of silver compounds with reducing agents. For example, reduced silver may be obtained by reduction of silver oxide with formalin in an alkaline solution, preferably in an aqueous solution of sodium carbonate.

The catalyst composition of the present invention contains at least one carbonate of a metal selected from the group consisting of the rare earth metals and yttrium and the carbonate is restricted to one obtained by the reaction of a chloride of a rare earth metal or yttrium (or mixtures thereof) with a carbonate or bicarbonate of alkali metal, or mixtures thereof. Of course, carbonates of rare earth metals or yttrium could be prepared from other kinds of salts of said metal such as nitrate or acetate, but surprisingly only carbonates prepared from chlorides have the unusual properties achieved by the catalyst of the present invention.

Examples of chlorides of rare earth metals or yttrium used in practice of the present invention are lanthanum chloride, cerium chloride, praseodymium chloride, neodymium chloride, samarium chloride, europium chloride, gadolinium chloride, terbium chloride, dysprosium chloride, holmium chloride, erbium chloride, thulium chloride ytterbium chloride, lutetium chloride, and yttrium chloride or mixtures thereof. Of these dysprosium chloride, holmium chloride, erbium chloride, ytterbium chloride, or yttrium chloride or mixtures thereof are preferably used.

Examples of the carbonates and bicarbonates of the alkali metal in the present invention are lithium carbonate, sodium carbonate, potassium carbonate, rubidium carbonate, cesium carbonate, sodium potassium carbonate, sodium bicarbonate, or potassium bicarbonate. Of these sodium carbonate or sodium bicarbonate or mixtures thereof are preferably used.

The reaction of a chloride of a rare earth metal or yttrium with a carbonate or bicarbonate of an alkali metal may be carried out in an aqueous solvent, preferably in water, and the reaction temperature may be in the range of about 0° to 100° C., preferably 1° to 40° C.

The amount of alkali metal carbonate or bicarbonate to be reacted with the chloride of the rare earth metal or yttrium is not restricted. Ordinarily about 0.1 to 30 mol equivalent carbonate or bicarbonate is used per mol of chloride, preferably about 0.5 to 5 mol equivalent. The reaction is preferably carried out by mixing an aqueous solution of a chloride of a rare earth metal or yttrium with an aqueous solution of a carbonate or bicarbonate of an alkali metal to yield a precipitate of a carbonate of the rare earth metal or yttrium, which is filtered and washed with water. The carbonate may be dried, but need not be dried, before use.

The preparation of the carbonate of the rare earth metal or yttrium is preferably effected in the presence of reduced silver in the reaction medium to yield a mixture of reduced silver and the rare earth metal or yttrium carbonate, in which the latter is well dispersed on the former.

At least one salt of a metal selected from the group consisting of alkali and alkaline earth metals is used as a promoter. Examples of such salts include the nitrates, sulfates, carbonates, nitrites, phosphates or hydroxides of the alkali or alkaline earth metals. Mixtures of potassium nitrate and barium nitrate are preferably used.

The catalyst carrier in the present invention is coated with reduced silver, the carbonate of the rare earth metal or yttrium, or mixtures thereof, and the salt of the alkali or alkaline earth metal, or mixtures thereof. Examples of catalyst carriers of the present invention include fused alumina, fused silica-alumina, silicon carbide, corundum, silicon, fused beryllium, magnesium-alumina spinel, sintered diatomaceous earth, brick pumice, graphite, silicon iron, silver plate, and aluminum powder. Preferably a carrier having a surface area in the range of 0.001 to 10 m$^2$/g is used. Fused alumina, fused silica-alumina or silicon carbide are preferably used. The form of the carrier is not restricted; spherical, ringed or pellet type carriers may be used. The size of the carrier is ordinarily in the range of about 1 to 10 mm diameter, preferably about 3 to 8 mm diameter.

The amount of reduced silver in the catalyst composition of the present invention is in the range of about 1 to 50 wt%, preferably about 5 to 30 wt%. The amount of rare earth metal or yttrium carbonate is not restricted, but is preferably in the range of about 0.05 to 10 mol% in relation to the mols of silver in the catalyst composition.

The amount of a promoter, a metal salt of alkali or alkaline earth metal, is not critical, but usually is within about 1 to 50 mol% based on the silver. Use of more than 50 mol% of the promoter is practical because further improvement of the catalyst is not resulted.

A preferred method of preparing the catalyst composition of the present invention is as follows:

Silver nitrate in water is allowed to react with sodium hydroxide in water to yield a precipitate of silver oxide which is filtered and washed with water. The silver oxide is added to an aqueous sodium carbonate solution with stirring to yield a slurried solution into which formalin is added dropwise with constant stirring. The reaction is preferably carried out at low temperature. The reduced silver may be dried (or not) before use.

The reduced silver is added to an aqueous solution of a chloride of a rare earth metal or yttrium and an aqueous solution of sodium carbonate or bicarbonate is added dropwise with stirring. After the reaction has been completed, the mixture of the reduced silver and the carbonate is filtered and washed with water. The mixture may or may not be dried before use. The mixture of the reduced silver and the carbonate is added to an aqueous solution of potassium nitrate or barium nitrate, for example, which serves as a promoter, and the product is mixed well to produce a slurry. To this slurry a catalyst carrier of fused silica-alumina is added and the mixture is heated at a temperature in the range of about 100° to 150° C. with occasional stirring to yield the catalyst composition.

In the oxidation of ethylene with a catalyst composition of the present invention, conventional reaction conditions can be used. The oxidation can be carried out under atmospheric or elevated pressure in the vapor or gaseous phase. Preferable pressures are in the range of about 5 to 30 kg/cm². The reaction temperature is in the range of about 150° to 350° C. and preferably about 200° to 260° C. A gaseous mixture containing ethylene and oxygen is fed to the catalyst bed. The gaseous mixture fed may contain nitrogen, carbon dioxide, argon, methane or ethane. Moreover, a so-called regulator such as 1,2-dichloroethane, vinyl chloride or chlorobenzene may be included.

The following Examples are introduced for the purpose of illustrating specific aspects of the present invention with no intention to limit the scope of the same, which is defined in the appended claims.

As used in the following Examples, the terms "selectivity" and "conversion" are defined by the following formulae:

$$\text{selectivity (\%)} = \frac{\text{mols of ethylene oxide produced}}{\text{mols of ethylene reacted}} \times 100$$

$$\text{conversion (\%)} = \frac{\text{mols of ethylene reacted}}{\text{mols of ethylene fed}} \times 100$$

The number of mols of ethylene reacted is calculated as the sum of the number of mols of ethylene converted to ethylene oxide and the number of mols of ethylene converted to carbon dioxide and water.

EXAMPLE 1

In a 6 liter flask, 339 g of silver nitrate were dissolved in 3 liters of distilled water and the solution was cooled to 4° C. by immersing the flask in a cold bath. A solution of 96 g of sodium hydroxide and 400 ml. of distilled water was cooled to 4° C. and added dropwise to the silver nitrate solution with stirring at such a rate that the temperature of the reaction mixture did not exceed 5° C. for about 30 minutes. After the reaction was completed, the precipitate of silver oxide was collected by filtration with a glass filter and washed with 10 liters of distilled water at a temperature of 4° C. In a separate 4 liter flask, 127 g of sodium carbonate were dissolved in 1.6 liters of distilled water and the flask was immersed in a cold bath to keep the temperature of the solution at 4° C. To this solution the filtered and washed silver oxide was added and the product was mixed well to provide a slurried solution. With 1 liter of distilled water 104 ml. of 37% formaline were diluted, cooled to 4° C., and added dropwise to the slurried solution with stirring at such a rate that the temperature of the reaction mixture did not exceed 5° C. for about 30 minutes. After the reaction was completed the precipitate of reduced silver was collected by filtration with a glass filter, washed with 10 liters of distilled water at a temperature of 4° C. and dried under reduced pressure.

In a 3 liter flask 13 g of reduced silver, 40.5 ml of 0.03 M yttrium chloride, and 1 liter of distilled water were mixed and the flask was immersed in a cold bath to keep the temperature of the mixture at 4° C. To this mixture 3.6 ml of 0.5 M sodium carbonate were added dropwise with stirring for 10 minutes. The mixture was stirred for another 10 minutes at 4° C. After the reaction was completed the mixture of reduced silver and carbonate of yttrium was collected by filtration with a glass filter, washed with 10 liters of distilled water at a temperature of 4° C., and dried under reduced pressure.

In a 100 ml. beaker 1.0 g of potassium nitrate and 1.3 g of barium nitrate were dissolved in 20 ml. of distilled water and 10.8 g of the mixture of reduced silver and carbonate of yttrium above obtained was added to the solution to give a slurried solution into which 42 g of a catalyst carrier (3/16 inch spheres, Alundum; SA5218, Norton Co.) were added and the mixture was heated in an oven at 105° C. with occasional stirring for about 15 hours. Then, the beaker was cooled to room temperature and a catalyst composition (Catalyst A-1) was obtained by separating the residual powder of reduced silver which was not coated on the catalyst carrier.

In the further Examples which follow, various catalyst compositions are shown with the use of abbreviations which indicate factors such as mol% of the chloride or other salt of the rare earth metal or yttrium to reduced silver, alkali carbonate or bicarbonate, (II) the mol ratio of the alkali carbonate or bicarbonate to the chloride or other salt (F/E), (III) mol% of promoters to reduced silver, (IV) kind of catalyst carrier, and (V) the silver content in the catalyst composition. Thus, for example, the catalyst A-1 appears in abbreviated form as follows:

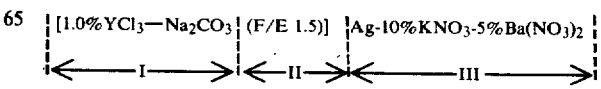

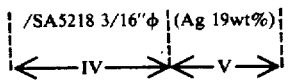

15 g of catalyst A-1 were placed in a glass tube having an internal diameter of 14 mm, and an ethylene-air mixture containing 5% by volume of ethylene and 95% by volume of air was passed continuously over the catalyst at a temperature of 240° C., at substantially atmospheric pressure, and at a rate of 100 ml of the ethylene-air mixture per minute under standard conditions of temperature and pressure (S.T.P.). The conversion per pass of ethylene and the selectivity to ethylene oxide are shown in Table 1 which appears hereinafter.

EXAMPLES 2–8

EXAMPLES 2–8

| Catalyst | Composition |
|---|---|
| A-2 | [1.0%SmCl₃-Na₂CO₃(F/E 1.5)]Ag-10%KNO₃-5% Ba(NO₃)₂/SA5218 3/16″φ (Ag 19 wt%) |
| A-3 | [1.0%GdCl₃-Na₂CO₃(F/E 1.5)]Ag-10%KNO₃-5% Ba(NO₃)₂/SA5218 3/16″φ (Ag 19 wt%) |
| A-4 | [1.0%DyCl₃-Na₂CO₃(F/E 1.5)]Ag-10%KNO₃-5% Ba(NO₃)₂/SA5218 3/16″φ (Ag 19 wt%) |
| A-5 | [1.0%ErCl₃-Na₂CO₃(F/E 1.5)]Ag-10%KNO₃-5% Ba(NO₃)₂/SA5218 3/16″φ (Ag 19 wt%) |
| A-6 | [1.0%TmCl₃-Na₂CO₃(F/E 1.5)]Ag-10%KNO₃-5% Ba(NO₃)₂/SA5218 3/16″φ (Ag 19 wt%) |
| A-7 | [1.0%YbCl₃-Na₂CO₃(F/E 1.5)]Ag-10%KNO₃-5% Ba(NO₃)₂/SA5218 3/16″φ (Ag 19 wt%) |
| A-8 | [1.0%LuCl₃-Na₂CO₃(F/E 1.5)]Ag-10%KNO₃-5% Ba(NO₃)₂/SA5218 3/16″φ (Ag 19 wt%). |

Oxidation of ethylene was carried out with these catalyst compositions by use of the same method as described in Example 1 and the results are shown in Table 1.

TABLE 1

| Example No. | Catalyst | Reaction time (hr) | Conversion (%) | Selectivity (%) |
|---|---|---|---|---|
| 1 | A-1 | 48 | 8.2 | 85.4 |
|   |     | 108 | 8.6 | 83.1 |
| 2 | A-2 | 48 | 4.0 | 81.6 |
|   |     | 108 | 4.2 | 82.1 |
| 3 | A-3 | 48 | 9.3 | 81.4 |
|   |     | 108 | 7.5 | 82.6 |
| 4 | A-4 | 48 | 7.1 | 85.0 |
|   |     | 168 | 8.5 | 84.1 |
| 5 | A-5 | 48 | 6.4 | 84.7 |
|   |     | 168 | 6.1 | 84.0 |
| 6 | A-6 | 48 | 10.4 | 86.2 |
|   |     | 168 | 10.7 | 85.3 |
| 7 | A-7 | 48 | 6.8 | 88.0 |
|   |     | 168 | 7.0 | 88.4 |
| 8 | A-8 | 48 | 7.5 | 86.4 |
|   |     | 168 | 7.9 | 86.4 |

EXAMPLES 9–11

Three catalyst compositions (Catalysts A-9 to A-11) were prepared with the use of potassium carbonate, rubidium carbonate, and cesium carbonate in the place of sodium carbonate by the same method as described in Example 1. Compositions of catalysts A-9 to A-11 are shown as follows:

| Catalyst | Composition |
|---|---|
| A-9  | [1.0%YCl₃-K₂CO₃(F/E 1.5)]Ag-10%KNO₃-5%Ba(NO₃)₂/SA5218 3/16″φ (Ag 19 wt %) |
| A-10 | [1.0%YCl₃-Rb₂CO₃(F/E 1.5)]Ag-10%KNO₃-5%Ba(NO₃)₂/SA5218 3/16″φ (Ag 19 wt%) |
| A-11 | [1.0%YCl₃-Cs₂CO₃(F/E 1.5)]Ag-10%KNO₃-5% Ba(NO₃)₂/SA5218 3/16″φ (Ag 19 wt%) |

Oxidation of ethylene was carried out by use of the same method as described in Example 1 and the results are shown in Table 2.

TABLE 2

| Example No. | Catalyst | Reaction time (hr) | Conversion (%) | Selectivity (%) |
|---|---|---|---|---|
| 9  | A-9  | 48  | 8.1  | 84.4 |
|    |      | 108 | 9.0  | 83.6 |
| 10 | A-10 | 48  | 9.6  | 84.6 |
|    |      | 108 | 10.2 | 83.5 |
| 11 | A-11 | 48  | 9.5  | 84.1 |
|    |      | 108 | 9.8  | 83.2 |

EXAMPLE 12

In a 4 liter flask 50 g of reduced silver which was obtained by use of the same method as described in Example 1, and 2 liters of distilled water were mixed to give a slurried solution and the flask was immersed in a cold bath to keep the temperature of the solution at 4° C. To this solution 15.6 ml of 0.3 M ytterbium chloride were added and 70 ml of 0.1 M sodium bicarbonate precooled to 4° C. were added dropwise with stirring for 10 minutes. The mixture was stirred for another 10 minutes at 4° C. After completing the reaction a mixture of reduced silver and carbonate of ytterbium was collected by filtration with a glass filter, washed with 10 liters of distilled water at a temperature of 4° C. and dried under reduced pressure.

In a 100 ml beaker, 0.37 g of potassium nitrate and 0.50 g of barium nitrate were dissolved in 20 ml of distilled water and the mixture of reduced silver and carbonate of ytterbium above obtained was added to the solution to give a slurried solution into which 30 g of a catalyst carrier (3×4 mm, Alundum; SA5105, Norton Co.) were added and the mixture was heated in an oven at 105° C. with occasional stirring for about 15 hours. Then, the mixture was cooled to room temperature and a catalyst composition (Catalyst A-12) was obtained separating the residual reduced silver which was not coated on the catalyst carrier. Catalyst A-12 is shown as follows:

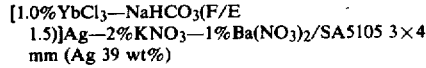

10 g of Catalyst A-12 were placed in a glass tube having an internal diameter of 14 mm, and an ethylene-air mixture containing 5% by volume of ethylene and 95% by volume of air was passed continuously over the catalyst at a temperature of 250° C., at substantially atmospheric pressure, and at the rate of 100 ml of the ethylene-air mixture per minute (S.T.P.). The results are shown in Table 3 which follows Examples 13–16.

EXAMPLES 13–16

Four catalyst compositions (Catalysts A-13 to A-16) were prepared by use of the same method as described in Example 12. The compositions of Catalysts A-13 to A-16 are shown as follows:

| Catalyst | Composition |
|---|---|
| A-13 | [1.0%YbCl$_3$-NaHCO$_3$(F/E 0.9)]Ag-2%KNO$_3$-1%Ba(NO$_3$)$_2$/SA5105 3 × 4 mm (Ag 39 wt%) |
| A-14 | [1.0%YbCl$_3$-NaHCO$_3$(F/E 3.0)]Ag-2%KNO$_3$-1%Ba(NO$_3$)$_2$/SA5105 3 × 4 mm (Ag 39 wt%) |
| A-15 | [1.0%YbCl$_3$-NaHCO$_3$(F/E 1.5)]Ag-10%KNO$_3$-5%Ba(NO$_3$)$_2$/SA5105 3 × 4 mm (Ag 39 wt%) |
| A-16 | [1.0%LuCl$_3$-NaHCO$_3$(F/E 1.5)]Ag-10%KNO$_3$-5%Ba(NO$_3$)$_2$/SA5105 3 × 4 mm (Ag 39 wt%) |

Oxidation of ethylene was carried out with these catalyst compositions by use of the same method as described in Example 12. The results are shown in Table 3.

TABLE 3

| Example No. | Catalyst | Reaction time (hr) | Conversion (%) | Selectivity (%) |
|---|---|---|---|---|
| 12 | A-12 | 48 | 19.9 | 84.6 |
|  |  | 168 | 23.8 | 83.7 |
| 13* | A-13 | 48 | 22.3 | 84.5 |
| 14 | A-14 | 48 | 19.0 | 86.4 |
|  |  | 168 | 18.5 | 86.5 |
| 15 | A-15 | 48 | 19.5 | 83.8 |
|  |  | 168 | 19.1 | 83.8 |
|  |  | 360 | 25.2 | 83.1 |
| 16 | A-16 | 48 | 17.9 | 84.4 |
|  |  | 108 | 16.6 | 84.5 |

*with 15 g catalyst at 240° C.

EXAMPLES 17–20

Four catalyst compositions (Catalysts A-17 to A-20) were prepared with the use of lanthanum chloride, cerium chloride, praseodymium chloride, and neodynium chloride in the place of ytterbium chloride by use of the same method as described in Example 12 using the catalyst carrier of Example 1.

The compositions of Catalysts A-17 to A-20 are shown as follows:

| Catalyst | Composition |
|---|---|
| A-17 | [1.0%LaCl$_3$-NaHCO$_3$(F/E 1.5)]Ag-10%KNO$_3$-5%Ba(NO$_3$)$_2$/SA5218 3/16"φ(Ag 28 wt%) |
| A-18 | [1.0%CeCl$_3$-NaHCO$_3$(F/E 1.5)]Ag-10%KNO$_3$-5%Ba(NO$_3$)$_2$/SA5218 3/16"φ(Ag 28 wt%) |
| A-19 | [1.0%PrCl$_3$-NaHCO$_3$(F/E 1.5)]Ag-10%KNO$_3$-5%Ba(NO$_3$)$_2$/SA5218 3/16"φ(Ag 28 wt%) |
| A-20 | [1.0%NdCl$_3$-NaHCO$_3$(F/E 1.5)]Ag-10%KNO$_3$-5%Ba(NO$_3$)$_2$/SA5218 3/16"φ(Ag 28 wt%) |

30 g of catalyst were placed in a glass tube having an internal diameter of 13 mm, and an ethylene-oxygen-nitrogen mixture containing 5% by volume of ethylene, 6.6% by volume of oxygen, and 88.4% by volume of nitrogen was passed continuously over the catalyst at a temperature of 240° C., at substantially atmospheric pressure, and at a rate of 100 ml of the ethylene-oxygen-nitrogen mixture per minute (S.T.P.). The results are shown in Table 4.

TABLE 4

| Example No. | Catalyst | Reaction time (hr) | Conversion (%) | Selectivity (%) |
|---|---|---|---|---|
| 17 | A-17 | 48 | 2.4 | 82.1 |
|  |  | 108 | 2.4 | 84.3 |
| 18 | A-18 | 48 | 2.1 | 84.1 |
|  |  | 108 | 2.6 | 83.9 |
| 19 | A-19 | 48 | 2.8 | 83.9 |
|  |  | 108 | 2.3 | 83.0 |
| 20 | A-20 | 48 | 5.1 | 85.6 |
|  |  | 108 | 5.0 | 84.4 |

EXAMPLES 21–23

Three catalyst compositions (Catalysts A-21 to A-23) were prepared by the use of europium chloride, terbium chloride, and holmium chloride in the place of lanthanum chloride by the same method as described in Example 17. The compositions of Catalysts A-21 to A-23 are shown as follows:

| Catalyst | Composition |
|---|---|
| A-21 | [1.0%EuCl$_3$-NaHCO$_3$(F/E 1.5)]Ag-10%KNO$_3$-5%Ba(NO$_3$)$_2$/SA5218 3/16"φ(Ag 28 wt%) |
| A-22 | [1.0%TbCl$_3$-NaHCO$_3$(F/E 1.5)]Ag-10%KNO$_3$-5%Ba(NO$_3$)$_2$/SA5218 3/16"φ(Ag 28 wt%) |
| A-23 | [1.0%HoCl$_3$-NaHCO$_3$(F/E 1.5)]Ag-10%KNO$_3$-5%Ba(NO$_3$)$_2$/SA5218 3/16"φ(Ag 28 wt%) |

Oxidation of ethylene was carried out with these catalyst compositions by use of the same method as described in Example 17 with the use of 20 g of the catalyst composition and at a rate of 200 ml of the ethylene-oxygen-nitrogen mixture per minute. The results are shown in Table 5.

TABLE 5

| Example No. | Catalyst | Reaction time (hr) | Conversion (%) | Selectivity (%) |
|---|---|---|---|---|
| 21 | A-21 | 48 | 3.3 | 86.3 |
|  |  | 108 | 2.6 | 85.4 |
| 22 | A-22 | 48 | 4.5 | 88.6 |
|  |  | 108 | 4.4 | 87.1 |
| 23 | A-23 | 48 | 3.4 | 89.6 |
|  |  | 108 | 2.8 | 89.7 |

EXAMPLES 24–26

Three catalyst compositions (Catalysts A-24 to A-26) were prepared by the use of ytterbium chloride in the place of europium chloride and by the use of potassium bicarbonate, sodium potassium carbonate and lithium carbonate in the place of sodium bicarbonate by use of the same method as described in Example 21. Compositions of Catalysts A-24 to A-26 are shown as follows:

| Catalyst | Composition |
|---|---|
| A-24 | [1.0%YbCl$_3$-KHCO$_3$(F/E 1.5)]Ag-10%KNO$_3$-5%Ba(NO$_3$)$_2$/SA5218 3/16"φ(Ag 28 wt%) |
| A-25 | [1.0%YbCl$_3$-NaKCO$_3$(F/E 1.5)]Ag-10%KNO$_3$-5%Ba(NO$_3$)$_2$/SA5218 3/16"φ(Ag 28 wt%) |
| A-26 | [1.0%YbCl$_3$-Li$_2$CO$_3$(F/E 1.5)]Ag-10%KNO$_3$-5%Ba(NO$_3$)$_2$/SA5218 3/16"φ(Ag 28 wt%) |

Oxidation of ethylene was carried out with these catalyst compositions by the same method as described in Example 21. The results are shown in Table 6.

TABLE 6

| Example No. | Catalyst | Reaction time (hr) | Conversion (%) | Selectivity (%) |
|---|---|---|---|---|
| 24 | A-24 | 48 | 3.9 | 90.4 |

TABLE 6-continued

| Example No. | Catalyst | Reaction time (hr) | Conversion (%) | Selectivity (%) |
|---|---|---|---|---|
|  |  | 72 | 3.8 | 90.4 |
| 25 | A-25 | 48 | 3.4 | 90.9 |
|  |  | 60 | 3.3 | 90.9 |
| 26 | A-26 | 48 | 3.6 | 90.6 |
|  |  | 60 | 3.8 | 89.7 |

EXAMPLES 27–31

Five catalyst compositions (Catalysts A-27 to A-31) were prepared by the use of potassium nitrate-strontium nitrate, sodium nitrate-barium nitrate, sodium nitrate, sodium phosphate, and potassium sulfate in the place of potassium nitrate-barium nitrate by use of the same method as described in Example 12. Compositions of Catalysts A-27 to A-31 are shown as follows:

| Catalyst | Composition |
|---|---|
| A-27 | [1.0%YbCl$_3$-NaHCO$_3$(F/E 1.5)]Ag-10%KNO$_3$-5%Sr(NO$_3$)$_2$/SA5105 3 × 4 mm (Ag 39 wt%) |
| A-28 | [1.0%YbCl$_3$-NaHCO$_3$(F/E 1.5)]Ag-10.5%NaNO$_3$-4.5%BA(NO$_3$)$_2$/SA5105 3 × 4 mm (Ag 39 wt%) |
| A-29 | [1.0%YbCl$_3$-NaHCO$_3$(F/E 1.5)]Ag-4%NaNO$_3$/SA5105 3 × 4 mm (Ag 39 wt%) |
| A-30 | [1.0%YbCl$_3$-NaHCO$_3$(F/E 1.5)]Ag-10%NaPO$_4$/SA5105 3 × 4 mm (Ag 39 wt%) |
| A-31 | [1.0%YbCl$_3$-NaHCO$_3$(F/E 1.5)]Ag-10%K$_2$SO$_4$/SA5105 3 × 4 mm (Ag 39 wt%) |

Oxidation of ethylene was carried out with these catalyst compositions by use of the same method as described in Example 12. The results are shown in Table 7.

TABLE 7

| Example No. | Catalyst | Reaction time (hr) | Conversion (%) | Selectivity (%) |
|---|---|---|---|---|
| 27 | A-27 | 48 | 11.3 | 77.7 |
|  |  | 240 | 11.0 | 81.6 |
| 28 | A-28 | 48 | 17.3 | 81.3 |
|  |  | 72 | 18.0 | 81.1 |
| 29* | A-29 | 48 | 17.5 | 87.0 |
|  |  | 120 | 18.0 | 86.7 |
| 30 | A-30 | 48 | 22.5 | 79.1 |
|  |  | 120 | 22.8 | 78.1 |
| 31 | A-31 | 48 | 13.8 | 71.1 |
|  |  | 120 | 21.8 | 76.7 |

*with 15 g catalyst at 240° C.

EXAMPLES 32 and 33

Two catalyst compositions (Catalysts A-32 and A-33) were prepared by the use of sodium nitrate or lithium nitrate in the place of the mixture of potassium nitrate and barium nitrate by the same method as described in Example 7. Compositions of Catalysts A-32 and A-33 are shown as follows:

| Catalyst | Composition |
|---|---|
| A-32 | [1.0%YbCl$_3$-Na$_2$CO$_3$(F/E 1.5)]Ag-10%NaNO$_3$/SA5218 3/16"φ(Ag 19 wt%) |
| A-33 | [1.0%YbCl$_3$-Na$_2$CO$_3$(F/E 1.5)]Ag-10%LiNO$_3$/SA5218 3/16"φ(Ag 19 wt%) |

Oxidation of ethylene was carried out with these catalyst compositions by use of the same method as described in Example 7. The results are shown in Table 8.

TABLE 8

| Example No. | Catalyst | Reaction time (hr) | Conversion (%) | Selectivity (%) |
|---|---|---|---|---|
| 32 | A-32 | 48 | 10.9 | 86.7 |
|  |  | 120 | 9.7 | 88.4 |
| 33 | A-33 | 48 | 11.2 | 78.2 |
|  |  | 96 | 13.5 | 76.9 |

EXAMPLE 34

The following catalyst composition (Catalyst A-34) was prepared by use of the same method as described in Example 1. This was done by using different amounts of yttrium chloride and sodium carbonate. Catalyst A-34 is shown as follows:

[0.3%YCl$_3$—Na$_2$CO$_3$(F/E 15)]Ag—2%KNO$_3$—1%Ba(NO$_3$)$_2$/SA5218 3/16"φ(Ag 21 wt%)

Oxidation of ethylene was carried out with Catalyst A-34 by use of the same method as described in Example 1. The results are shown in Table 9.

TABLE 9

| Example No. | Catalyst | Reaction time (hr) | Conversion (%) | Selectivity (%) |
|---|---|---|---|---|
| 34 | A-34 | 48 | 7.8 | 83.3 |
|  |  | 96 | 8.2 | 83.2 |
| 35 | B-1 | 48 | 3.8 | 73.2 |
|  |  | 96 | 3.0 | 73.1 |
| 36 | B-2 | 48 | 12.3 | 57.3 |
|  |  | 96 | 17.2 | 71.0 |

COMPARATIVE EXAMPLES 35 and 36

Two comparative catalyst compositions (Catalysts B-1 and B-2) were prepared with the use of sodium fluoride or sodium phosphate in the place of sodium carbonate by use of the same method as described in Example 34. Compositions of Catalysts B-1 and B-2 are shown as follows:

| Catalyst | Composition |
|---|---|
| B-1 | [0.3%YCl$_3$-NaF(F/E 30)]Ag-2%KNO$_3$-1%Ba(NO$_3$)$_2$/SA5218 3/16"φ(Ag 21 wt%) |
| B-2 | [0.3%YCl$_3$-Na$_3$PO$_4$(F/E 10)]Ag-2%KNO$_3$-1%Ba(NO$_3$)$_2$/SA5218 3/16"φ(Ag 21 wt%) |

Oxidation of ethylene was carried out with these catalyst compositions by use of the same method as described in Example 34. The results are shown in Table 9.

COMPARATIVE EXAMPLES 37–40

In a 150 ml beaker, 21.6 g of reduced silver which was obtained by use of the same method as described in Example 1 was mixed with 50 ml of distilled water to yield a slurry. Into this slurry 42 g of a catalyst carrier (3/16" spheres, Alundum; SA5218, Norton Co.) were added. The mixture was heated in an oven at 105° C. with occasional stirring for about 15 hours and then the mixture was cooled to room temperature to produce a catalyst composition (Catalyst B-3) by separating out the residual reduced silver which was not coated on the carrier. Three catalyst compositions (Catalysts B-4 to B-6) were prepared by the same method with the use of distilled water containing potassium nitrate and barium nitrate. Compositions of Catalysts B-3 to B-6 are shown as follows:

| Catalyst | Composition |
|---|---|
| B-3 | Ag/SA5218 3/16"φ(Ag 28 wt%) |
| B-4 | Ag-2%KNO₃-1%Ba(NO₃)₂/SA5218 3/16"φ(Ag 28 wt%) |
| B-5 | Ag-4%KNO₃-2%Ba(NO₃)₂/SA5218 3/16"φ(Ag 28 wt%) |
| B-6 | Ag-10%KNO₃-5%Ba(NO₃)₂/SA5218 3/16"φ(ag 28 wt%) |

Oxidation of ethylene was carried out with these catalyst compositions by use of the same method as described in Example 21. The results are shown in Table 10.

TABLE 10

| Example No. | Catalyst | Reaction time (hr) | Conversion (%) | Selectivity (%) |
|---|---|---|---|---|
| 37 | B-3 | 24 | 50.7 | 32.7 |
|  |  | 48 | 50.9 | 38.6 |
| 38 | B-4 | 24 | 18.4 | 51.7 |
|  |  | 48 | 19.7 | 51.8 |
| 39 | B-5 | 24 | 1.2 | 24.4 |
|  |  | 48 | 1.4 | 30.7 |
| 40 | B-6 | 24 | <0.5 | — |
|  |  | 48 | <0.5 | — |

COMPARATIVE EXAMPLES 41 and 42

Two comparative catalyst compositions (Catalysts B-7 and B-8) were prepared with the use of ytterbium nitrate and ytterbium acetate in the place of ytterbium chloride by the same method as described in Example 21. Compositions of Catalysts B-7 and B-8 are shown as follows:

| Catalyst | Composition |
|---|---|
| B-7 | [1.0%Yb(NO₃)₃-NaHCO₃(F/E 1.5)]Ag-10%KNO₃-5%Ba(NO₃)₂/SA5218 3/16"φ(Ag 28wt%) |
| B-8 | [1.0%Yb(CH₃CO₂)₃-NaHCO₃(F/E 1.5)]Ag-10%KNO₃-5%Ba(NO₃)₂/SA5218 3/16"φ(Ag 28 wt%) |

Oxidation of ethylene was carried out with these catalyst compositions by use of the same method as described in Example 21. The results are shown in Table 11.

TABLE 11

| Example No. | Catalyst | Reaction time (hr) | Conversion (%) | Selectivity (%) |
|---|---|---|---|---|
| 41 | B-7 | 24 | 2.5 | 18.3 |
|  |  | 48 | 1.9 | 17.7 |
| 42 | B-8 | 24 | 1.9 | 20.0 |
|  |  | 48 | 1.7 | 23.0 |

I claim:

1. A catalyst composition for the oxidation of ethylene to ethylene oxide which comprises the combination of reduced silver (A) and at least one carbonate (B) of a metal selected from the group consisting of rare earth metals and yttrium, said carbonate being prepared by the reaction of a chloride of a metal selected from the group consisting of the rare earth metals and yttrium and mixtures thereof with a carbonate or bicarbonate of an alkali metal or mixture thereof, said reduced silver (A) and said carbonate (B) being supported together with at least one salt (C) of a metal selected from the group consisting of the alkali and alkaline earth metals and mixtures thereof on a catalyst carrier (D) having a surface area of less than about 10 m²/g.

2. The catalyst composition of claim 1, wherein the reduced silver is prepared by reducing silver oxide with formalin in aqueous solution.

3. The catalyst composition of claim 1, wherein the chloride is lanthanum chloride.

4. The catalyst composition of claim 1, wherein the chloride is cerium chloride.

5. The catalyst composition of claim 1, wherein the chloride is praseodymium chloride.

6. The catalyst composition of claim 1, wherein the chloride is neodymium chloride.

7. The catalyst composition of claim 1, wherein the chloride is samarium chloride.

8. The catalyst composition of claim 1, wherein the chloride is europium chloride.

9. The catalyst composition of claim 1, wherein the chloride is gadolinium chloride.

10. The catalyst composition of claim 1, wherein the chloride is terbium chloride.

11. The catalyst composition of claim 1, wherein the chloride is dysprosium chloride.

12. The catalyst composition of claim 1, wherein the chloride is holmium chloride.

13. The catalyst composition of claim 1, wherein the chloride is erbium chloride.

14. The catalyst composition of claim 1, wherein the chloride is thulium chloride.

15. The catalyst composition of claim 1, wherein the chloride is ytterbium chloride.

16. The catalyst composition of claim 1, wherein the chloride is lutetium chloride.

17. The catalyst composition of claim 1, wherein the chloride is yttrium chloride.

18. The catalyst composition of claim 1, wherein the carbonate is sodium carbonate.

19. The catalyst composition of claim 1, wherein the carbonate is potassium carbonate.

20. The catalyst composition of claim 1, wherein the carbonate is lithium carbonate.

21. The catalyst composition of claim 1, wherein the carbonate is cesium carbonate.

22. The catalyst composition of claim 1, wherein the carbonate is rubidium carbonate.

23. The catalyst composition of claim 1, wherein the carbonate is sodium potassium carbonate.

24. The catalyst composition of claim 1, wherein the bicarbonate is sodium bicarbonate.

25. The catalyst composition of claim 1, wherein the bicarbonate is potassium bicarbonate.

26. The catalyst composition of claim 1, wherein the salt (C) is a mixture of sodium nitrate and potassium nitrate.

27. The catalyst composition of claim 1, wherein the salt (C) is a mixture of potassium nitrate and strontium nitrate.

28. The catalyst composition of claim 1, wherein the salt (C) is a mixture of sodium nitrate and barium nitrate.

29. The catalyst composition of claim 1, wherein the salt (C) is sodium nitrate.

30. The catalyst composition of claim 1, wherein the salt (C) is sodium phosphate.

31. The catalyst composition of claim 1, wherein the salt (C) is potassium sulphate.

32. The catalyst composition of claim 1, wherein the composition is prepared by coating a carrier (D) with a slurried solution which contains the reduced silver (A), the carbonate (B) and the salt (C) and drying the coated carrier.

33. The catalyst composition of claim 32, wherein the reduced silver (A) and the carbonate (B) are previously combined by immersing the reduced silver into an aqueous solution of a chloride of a metal selected from the group consisting of rare earth metal and yttrium, adding thereto an aqueous solution of a carbonate or bicarbonate of alkali metal thereby converting said chloride into the insoluble carbonate and precipitating it on the reduced silver, filtering off the combined reduced silver and precipitated carbonate, and washing with water.

34. The catalyst composition of claim 1, wherein the amount of said reduced silver (A) is about 1–50% by weight, the amount of said carbonate (B) of rare earth metal or yttrium is about 0.05–10 mol % in relation to the mols of silver, and the amount of said salt (C) is about 1 to 50 mol % based on said silver (A).

35. The catalyst composition of claim 34, wherein the amount of said reduced silver (A) is about 5–30% by weight.

36. The catalyst composition of claim 1, including a catalyst carrier (D) having a surface area of less than about 10 m$^2$/g.

37. The catalyst composition of claim 36, wherein the carrier (D) is a fused silica alumina.

38. In a method of making a catalyst of claim 1, the steps which comprise providing a carrier (D), coating the carrier (D) with a slurried solution which contains the reduced silver (A), the carbonate (B) and the salt (C) and drying the coated carrier.

39. In a method of making a catalyst of claim 38 wherein the slurried solution containing said reduced silver (A) and said carbonate (B) is prepared by immersing the reduced silver into an aqueous solution of a chloride of a metal selected from the group consisting of rare earth metal and yttrium, and mixtures thereof, adding thereto an aqueous solution of a carbonate or bicarbonate of alkali metal or mixtures thereof, thereby converting said chloride into the insoluble carbonate and precipitating it on the reduced silver, filtering off the combined reduced silver and precipitated carbonate and washing with water.

40. In a method of oxidizing ethylene to ethylene oxide, the steps which comprise contacting and reacting said ethylene and a source of oxygen at an elevated temperature in contact with the catalyst of claim 1.

41. The catalyst composition of claim 1 wherein the salt (C) is a mixture of potassium nitrate and barium nitrate.

* * * * *